United States Patent [19]

Smith

[11] 4,323,077
[45] Apr. 6, 1982

[54] ACOUSTIC INTENSITY MONITOR

[75] Inventor: Lowell S. Smith, Schenectady, N.Y.

[73] Assignee: General Electric Company, Schenectady, N.Y.

[21] Appl. No.: 129,689

[22] Filed: Mar. 12, 1980

[51] Int. Cl.³ .............................................. A61B 10/00
[52] U.S. Cl. ..................................... 128/660; 128/736
[58] Field of Search ..................... 128/24 A, 660-663, 128/736, 399-403, 804; 23/230 LC; 73/356, 606, 644; 252/299, 315-317

[56] References Cited

U.S. PATENT DOCUMENTS

| 3,169,254 | 2/1965 | Davis | 117/72 X |
|---|---|---|---|
| 3,533,399 | 10/1970 | Goldberg et al. | 128/736 X |
| 3,578,844 | 5/1971 | Churchill et al. | 252/316 X |
| 3,585,381 | 6/1971 | Hodson | 250/47 X |
| 3,697,297 | 10/1972 | Churchill et al. | 252/299 |
| 3,732,119 | 5/1973 | Churchill et al. | 252/316 X |
| 4,002,221 | 1/1977 | Buchalter | 128/660 |
| 4,080,959 | 3/1978 | LeVeen | 128/736 |
| 4,190,058 | 2/1980 | Sagi | 128/736 |
| 4,211,949 | 7/1980 | Brishen | 310/322 |

FOREIGN PATENT DOCUMENTS

| 901277 | 5/1972 | Canada | 252/299 |
|---|---|---|---|
| 899610 | 9/1972 | Canada | 252/299 |
| 912806 | 10/1972 | Canada | 252/299 |

Primary Examiner—Robert W. Michell
Assistant Examiner—Francis J. Jaworski
Attorney, Agent, or Firm—Donald R. Campbell; James C. Davis, Jr.; Marvin Snyder

[57] ABSTRACT

A system and method are disclosed for monitoring the acoustic intensity of ultrasonic energy applied to a body by an ultrasonic probe for the purpose of diagnosing an internal target. The probe contacts a limited area of the body skin and a coupling medium, such as a coupling gel, is interposed to enhance acoustic coupling between the probe and the skin. A thermally sensitive agent in the coupling medium imparts color to the latter indicative of the heat dissipated on the skin area under the probe. Whenever a predetermined color change of the coupling medium indicates that the heat dissipation on this area exceeds a predetermined limit, the acoustic intensity of the ultrasonic energy beamed to the target is reduced.

13 Claims, 2 Drawing Figures

ACOUSTIC INTENSITY MONITOR

The present invention relates to a new and improved system and method for monitoring the acoustic intensity of ultrasonic energy applied to a body, in particular to a system and method wherein an acoustic coupling medium is employed which includes a thermally sensitive agent to provide a visual indication of the temperature of the medium and thus of the acoustic intensity of the applied energy.

BACKGROUND OF THE INVENTION

In the diagnosis of a body by ultrasonic techniques, e.g. in the examination of the human body, ultrasonic energy radiated at the body is beamed to an internal target. Typically, a diagnostic probe is used in which a single crystal or an array of ultrasonic transducers is positioned behind the probe wear plate. The external surface of the wear plate is placed substantially in contact with a limited area of the patient's skin and a coupling medium is interposed between them which may take the form of a gel deposited as a thin coating on the skin area. The purpose of the coupling gel is to enhance acoustic coupling between the wear plate surface and the skin.

When the probe and other associated power equipment are operating normally, the probe beams relatively low levels of ultrasonic energy to the target, e.g. on the order of 10 milliwatts/cm$^2$ averaged over both space and time. Under unusual circumstances, e.g. as a result of faulty operation or mishandling of the equipment, a malfunction or failure of the equipment may occur without knowledge of the patient or of the diagnostician. If the malfunction is such as to raise the acoustic intensity of the energy beamed to the target, a potential for harm to the patient may exist through thermal damage to the body or through ultrasonic cavitation. Thus, it becomes desirable to monitor the acoustic intensity of the applied energy on a continuous basis during the diagnostic procedure. This is especially important where the diagnostician, though medically trained, lacks the necessary technical training to distinguish between normal probe operation and an equipment malfunction. The monitoring procedure must therefore be simple and direct and provide an indication of equipment malfunction whenever the acoustic intensity of the applied ultrasonic energy exceeds a predetermined safety limit.

The use of thermographic techniques, whereby a liquid crystal material is applied to the skin and the color of the material is observed to provide an indication of skin temperature, is well established as a diagnostic tool. For example, mixtures of cholesteric liquid crystals such as cholesteryl oleyl carbonate, cholesteryl nonanoate, and cholesteryl benzoate, as disclosed in U.S. Pat. No. 3,533,399, show selective reflection near body skin temperatures that are visible as color changes to the eye of an observer. Where the liquid crystal material consists of a cream, it may be placed directly on the skin. However, the ability to observe the change of color of the material may be enhanced under certain conditions if the skin is first darkened with a water soluble dye, or with carbon black, in order to reduce extraneous reflections. As disclosed in U.S. Pat. No. 3,619,254, the material may also be silk screen printed onto the skin, e.g. by painting the skin through a silk screen, in order to control the thickness and uniformity of the coating so applied. An acrylic layer may be applied on top of the liquid crystal coating material for protection against degradation by the ambient air or by exposure to light. There also exist liquid crystal tapes which adhere directly to the skin.

The observation of color changes of the liquid crystal material may also be enhanced by applying the material on a substrate, such as a black-pigmented matrix or lattice, or on black polymer film, as disclosed in French Pat. No. 2,110,505 and Canadian Pat. No. 912,806, respectively. Where a liquid crystal tape is used, the tape may include a non-liquid crystal dye of a color adapted to improve the selective reflection of a particular color range, e.g. as taught by German Offenlegungsschrift Nos. 2,018,028 and 2,059,789 or by Canadian Pat. No. 901,277. It is also possible to compound a cream consisting of microencapsulated liquid crystals, carbon black and a surfactant in a water soluble organic solvent such as polyvinyl alcohol, as shown by Canadian Pat. No. 899,610. Such a cream will dry to a tough film and can be peeled off after use.

The encapsulation of the liquid crystal material may be carried out in a number of different ways. For example, small drops of the liquid crystal material may be dispersed in an aqueous mixture of gelatin and gum arabic to form a colloid. The coating that is formed when this mixture is applied to a surface such as the skin, can be hardened by the use of a diol such as perteredrol, or by a dialdehyde, e.g. formaldehyde. Various ways of carrying out the latter technique are disclosed in U.S. Pat. Nos. 3,697,297; 3,732,119; 3,585,381; and 3,578,844. However, the encapsulation of liquid crystals is not limited to the use of colloids. For example, a plastic such as polyurethane may be used to form the capsules. Each capsule so formed then comprises a plastic sheath containing a plurality of liquid crystals, e.g. as disclosed in Japanese Pat. Nos. 44,177 (1973) and 71,377 (1973).

As previously mentioned, the mechanism that produces the apparent color of the substance is selective reflection, whereby light of a particular color is reflected back strongly while other colors are substantially absorbed. This effect is due to the ordering of planes of the liquid crystal molecules and the spacing between these planes, i.e. the repeat distance between planes related to the same color. The extent by which the spacing of the repeat distance varies for a change of color covering the entire spectrum, i.e. from red through yellow to blue, may be no more than a factor of 2. Thus, only a small temperature change is required to produce the aforesaid color change if the liquid crystal material is properly selected. For example, cholesteryl oleyl carbonate is capable of traversing the entire color spectrum, i.e. for red to blue, in response to a temperature change of less than 1° C.

The use of liquid crystal materials of the kind mentioned above, particularly where the human body is concerned, has been largely limited in the past to thermographic applications, as discussed earlier. The present invention makes use of these materials to monitor the acoustic intensity of ultrasonic energy applied to a body for the purpose of diagnosing an internal target therein. As such it is capable of providing an indication of an equipment malfunction, which indication can be readily recognized even by a person lacking in technical training.

OBJECTS OF THE INVENTION

It is a primary object of the present invention to provide a simple and direct system and method for monitoring the acoustic intensity of ultrasonic energy applied to a body for diagnostic purposes, to prevent harm through thermal damage or through ultrasonic cavitation.

It is another object of the present invention to provide a monitoring system and method which enables personnel lacking extensive technical training to detect and equipment malfunction during the application of ultrasonic energy to a body.

It is a further object of the present invention to provide a system and method for preventing thermal damage or damage from ultrasonic cavitation to a body, wherein a continuous visual indication is provided of the acoustic intensity of ultrasonic energy applied to the body.

It is still another object of the present invention to provide a coupling medium for enhancing acoustic coupling between an ultrasonic probe and the external surface of a body with which the probe makes substantial contact, wherein a thermally sensitive agent incorporated in the medium provides an indication through a color change whenever the acoustic intensity of the ultrasonic energy applied to the body exceeds a predetermined limit.

These and other objects of the present invention together with the features and advantages thereof will become apparent from the following detailed specification when read in conjunction with the accompanying drawings.

DESCRIPTION OF THE INVENTION

Figure 1:
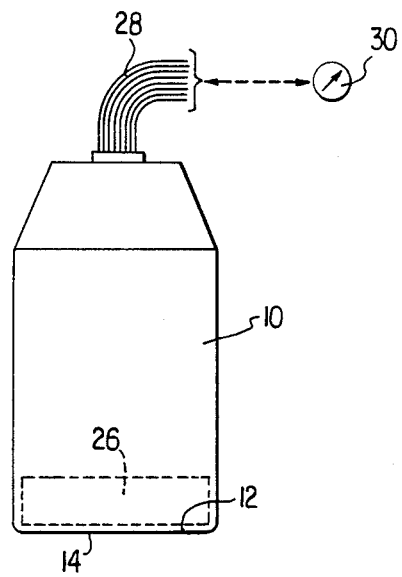
FIG. 1 illustrates a typical ultrasonic probe of the kind used in the present invention.

With reference now to the drawings, FIG. 1 shows a typical ultrasonic probe 10 of the type used in the medical diagnosis of a target in a patient's body by the application of ultrasonic energy thereto. Either a single ultrasonic transducer or an array of such transducers may be used, both being designated by the reference numeral 26. For purposes of the present discussion, a transducer array is assumed, which is adapted to be suitably energized through a cable 28 to radiate pulses of ultrasonic energy through a wear plate 12 on the lower end of the probe. The external wear plate surface 14, which may have a relatively small surface, e.g. measuring 1.5 cm $\times$ 2 cm, is adapted to make contact with a limited area on the patient's skin.

Figure 2:
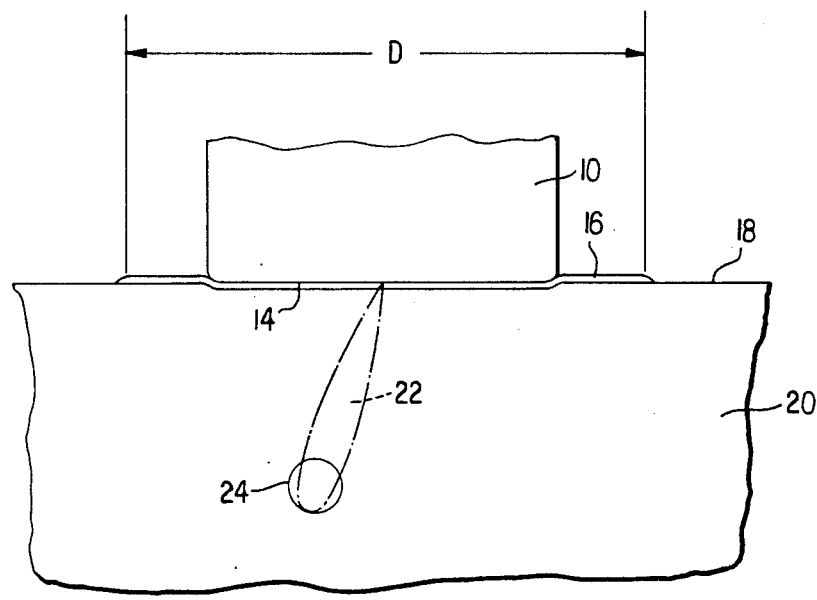
FIG. 2 illustrates a monitoring system and method of operation in accordance with the present invention.

The excitation of individual transducers of array 26 is phased to radiate a beam 22 of ultrasonic energy from the center of surface 14 into the patient's body 20, as illustrated schematically in FIG. 2. By suitably varying the phasing of the transducers, the direction of the beam may be changed within a limited angle so that the energy may be radiated to any selected target 24 in the patient's body within range of the beam. A dial adjustment, schematically illustrated at 30, is adapted to selectively set the level of radiated energy to any desired level of acoustic intensity, down to zero.

Between successive applications of pulses by ultrasonic transducer array 26, echoes reflected from the target are received by the array where they are sensed and transmitted as electrical signals. Signal transmission from the probe occurs by way of cable 28 to suitable apparatus for processing and conversion into a visual image of the target. Typically the target image appears on a CRT or similar display where it is observed by the attending diagnostician while the probe is moved about on the patient's body.

In operating the monitoring system in accordance with the present invention, probe 10, shown partially in FIG. 2, is positioned substantially in contact with the patient's body 20 and an acoustic coupling medium 16 is positioned between the external wear plate surface 14 and surface 18 of the patient's skin. As discussed above, the use of a coupling medium in order to enhance acoustic coupling between the probe and the patient's skin is well known in the art, the medium typically taking the form of a gel deposited as a thin coating on the skin. In accordance with the principles of the present invention, the gel includes a thermally sensitive agent which provides a visual indication of the heat dissipated on the skin area contacted by probe 10 as a result of the ultrasonic energy radiated to the body. Under normal operating conditions, this heat dissipation may be on the order of $10^2$ watt per $cm_2$ and thus well within the limits of safety. However, if the probe were to malfunction, e.g. if it were to operate in a failure mode, the heat dissipation on the skin may rise to a level as high as 0.5 watt per $cm^2$, i.e. up to fifty times the normal level. The visual indication provided under these conditions by the thermally sensitive agent, signals an acoustic intensity of the radiated energy sufficiently high to let thermal damage occur in the body, perhaps without knowledge of either the patient or the diagnostician.

In a preferred embodiment of the invention the gel includes cholesteric liquid crystals such as cholesteryl oleyl carbonate cholesteryl nonanoate, cholesteryl benzonate, or the like, whose molecular alignment depends on the temperature of the gel itself. These liquid crystals are selected such that a small temperature change produces a visually observable change in the primary color of reflected light.

The gel is deposited as a coating on a portion of skin surface 18, which has the approximate dimensions of the limited skin area to which probe 10 is applied, or which covers a somewhat larger area. The gel thus acts as a sensitive indicator of the heat dissipated on the skin area under the probe and hence of the acoustic beam intensity of the energy radiated to the selected target in the body.

The liquid crystals may be incorporated into the gel in different ways, using some of the known techniques discussed above. For example, the cholesteric liquid crystal molecules may be mixed into a water-soluble gel of the kind commercially available under the names of "Aquasonic" or "Ultraphonic". In one embodiment of the invention the liquid crystal molecules are encapsulated in a colloid or in a plastic sheath, each capsule having a diameter of approximately 10 microns and containing approximately $10^{12}$ liquid crystal molecules. A large number of such capsules is dispersed throughout the gel to provide it with a substantially uniform coloration. In still another embodiment of the invention, the gel may constitute a compound consisting entirely of cholesteric liquid molecules.

The combination of the probe and the gel in its simplest form constitutes a monitoring system in accordance with the principles of the present invention, which enables a user who lacks the necessary technical training to operate the diagnostic equipment in a manner that assures the safety of the patient even if an equipment malfunction were to occur. As previously stated, gel 16 is applied as a substantially uniform, thin coating to a limited area of the patient's skin which is to be contacted by the ultrasonic probe. Although the gel coating may be deposited directly on the patient's skin, it may be advantageous to darken the skin first by means of a substrate such as a dye, or carbon black, or the like, in order to enhance the observation of color changes of the gel. Alternatively, the substrate may consist of a black-pigmented lattice or of a black polymer film, all as discussed above.

In lieu of applying the gel directly to the skin, (with or without a substrate), an alternative method of application is to place the gel first on external wear plate surface 14 of the probe. Subsequently the gel-carrying probe surface is brought into sliding contact with the desired skin area to establish the coating on the latter. Still another method calls for applying the gel to the skin through a silk screen or the like, in order to obtain an even gel thickness. In either case, the coating is applied substantially uniformly to a thickness of preferably less than approximately 0.05 millimeter.

Under ordinary conditions, the gel is at room temperature when it is first applied to the skin of the patient, the latter normally being at a higher temperature. Warming of the gel coating to skin temperature occurs relatively quickly and uniformly due to the thinness and uniformity of the coating. This change of the temperature of the gel coating produces a corresponding color change. Therefore, before the diagnosis can proceed the gel color must be stabilized. This occurs when the gel coating stabilizes to the patient's initial skin temperature. The temperature-stabilized color then becomes the base or reference color to which subsequent color changes of the gel are compared.

It will be understood that skin temperature may vary from person to person. Further, a sick person may have a higher skin temperature than one who is well, and may even show significant temperature differences between different parts of the body. Thus, the same gel applied to different persons, or to different skin areas of the same person, may stabilize at different reference colors. This variation can be accommodated by the diagnostician by having recourse to a color chart on which the temperature-stabilized reference color of the gel is marked. Any color change of the gel relative to the reference color so marked on the chart is then monitored. Alternatively, a set of separate coupling gels or gel samples may be provided, each containing a thermally sensitive agent tailored to reach the same reference color at a different temperature. A range of body temperatures can thus be accommodated and the selection of the appropriate coupling gel will depend on matching the gel to the initial temperature of the limited skin area on which its gel is to be deposited. Since the temperature-stabilized reference color will be substantially the same regardless of which coupling gel is selected from the set, only the color change relative to the reference color needs to be monitored during the interval when ultrasonic energy is applied to the body.

After the gel color has been stabilized to its reference color, probe 10 is positioned so that external wear plate surface 14 is substantially in contact with the selected limited skin area of the patient on which gel coating 16 has been deposited. When the probe is turned on, ultrasonic energy is radiated to target 24 in the patient's body. Normal diagnostic procedure calls for moving the probe around on the aforesaid limited skin area. The diameter D of this area may vary from approximately 15 cm to as much as 30 cm, depending on the diagnostician. This is approximately the extent of the skin area covered by gel coating 16, as shown in FIG. 2. However, the skin portion on which the gel is deposited may be somewhat larger in practice, as explained above.

While ultrasonic energy is radiated to the body and probe 10 is moved around on the gel-coated skin area, different portions of the gel coating come into view. If the heat dissipated on the area under the probe were to exceed a predetermined limit, e.g. 0.1 watt per $cm^2$, a visually observable, predetermined color change of the gel will occur. Such a change would indicate to the diagnostician that the acoustic intensity of the energy radiated to the target in the body is in excess of a predetermined safe limit. In response, dial adjustment 30 may be varied to reduce the acoustic intensity, if necessary to zero. Thus, the color change exhibited by the gel coating as a result of the heat dissipated on the skin surface, permits the acoustic intensity of the ultrasonic energy radiated to the body and beamed to the internal body target to be monitored on a continuous basis.

The system and method which constitute the present invention are not limited to the monitoring of the maximum ultrasonic energy intensity level during medical diagnosis. They are likewise applicable to situations where other bodies or objects are examined by means of ultrasonic radiation and may be used to hold the intensity of the radiated energy between predetermined upper and lower limits. Depending on the ambient conditions at the start of the examination, the external surface of the diagnosed object may be at any temperature (higher or lower) with respect to the room temperature at which the gel resides. Account must be taken of these differences when stabilizing to the reference color.

From the foregoing discussion it will be apparent that numerous modifications, substitutions or equivalents will now occur to those skilled in the art all of which fall within the spirit and scope of the invention herein. Accordingly, it is intended that the invention be limited only by the scope of the appended claims.

What is claimed is:

1. A method monitoring the acoustic intensity of energy applied to a body by an ultrasonic probe, comprising the steps of:

positioning a coupling medium between mutually facing, external surfaces of said body and said probe adapted to enhance acoustic coupling between said surfaces, said coupling medium incorporating therein a thermally sensitive agent adapted to provide an indication corresponding to the temperature to which said medium is subjected;

stabilizing said coupling medium to the initial temperature of said body surface;

placing said probe surface substantially in contact with a limited area of said body surface while said coupling medium is positioned therebetween;

radiating ultrasonic energy to said body by means of said probe, said radiated energy being adapted to dissipate heat on said limited area of said body surface; and adjusting the acoustic intensity of said radiated energy when said temperature indication falls outside a predetermined range;

whereby the acoustic intensity of the ultrasonic energy applied to said body is monitored through the effect on said thermally sensitive agent produced by the heat dissipated on said limited body surface area;

wherein said thermally sensitive agent determines the color of said coupling medium in accordance with the temperature of the latter such that temperature changes to which said medium is subjected produce corresponding visually observable color changes; and wherein the stabilization of said medium includes the step of stabilizing the color of said medium to a reference color determined by the initial temperature of said limited body surface area.

2. The method in accordance with claim 1 wherein the adjustment of the acoustic intensity of said radiated ultrasonic energy comprises the step of decreasing said intensity upon the occurrence of a predetermined color change of said coupling medium relative to said reference color;

whereby the level of said ultrasonic energy applied to said body is maintained below a predetermined limit.

3. The method in accordance with claim 2 wherein said acoustic intensity is decreased to zero upon the occurrence of a color change of said coupling medium indicative of an equipment failure condition.

4. The method in accordance with claim 3 wherein said coupling medium comprises a coupling gel; and wherein the positioning of said medium between said mutually facing surfaces comprises the step of depositing a thin coating of said gel substantially on said external body surface to cover at least said limited body surface area, said gel being adapted to provide the desired acoustic coupling in said limited area between said probe and said body surface.

5. The method in accordance with claim 4 and further including the step of placing a black-pigmented thin substrate directly on said body surface to cover at least said limited area, said gel being deposited over said substrate;

whereby the observation of color changes of said gel is enhanced.

6. The method in accordance with claim 4 wherein the deposition of said gel coating on said body surface includes the steps of:

applying said gel to said external probe surface; and bringing the gel-carrying probe surface into sliding contact substantially with said body surface to distribute said gel on the latter at least over said limited area.

7. The method in accordance with claim 4 wherein the deposition of said gel coating substantially on said body surface includes the step of applying said coating in a substantially uniform thickness of less than approximately 0.05 millimeter;

whereby said gel coating is enabled rapidly and uniformly to reach said initial body surface temperature.

8. The method in accordance with claim 4 wherein said coupling medium is selected from one of a set of separate coupling gels, each of said gels including a thermally sensitive agent adapted to impart said reference color to the selected gel at a different temperature;

whereby the selected gel is chosen to match said initial temperature of said limited body surface area.

9. The method in accordance with claim 4 wherein said thermally sensitive agent comprises cholesteric liquid crystals having a molecular alignment dependent on the temperature of said gel and determinative of the primary color of light reflected by said crystals.

10. The method in accordance with claim 9 wherein said gel consists substantially exclusively of cholesteric liquid crystals.

11. The method in accordance with claim 9 wherein said gel includes a plurality of capsules carried in colloidal suspension, each of said capsules comprising a plurality of said liquid crystals, said capsules being dispersed throughout said gel to provide a substantially uniform gel color determined by the temperature of said gel.

12. The method in accordance with claims 4 or 9 wherein said ultrasonic energy is applied to the human body to diagnose a target therein on which said energy is focused; and wherein said gel coating is applied to a limited surface area of the body skin substantially contacted by said probe;

whereby the level of the energy radiated to said target is monitored through the effect on said gel coating of the heat dissipated on said limited surface area of the skin.

13. A method of monitoring the acoustic intensity of energy applied to a body by an ultrasonic probe, comprising the steps of:

positioning a coupling medium between mutally facing, external surfaces of said body and probe to enhance acoustic coupling between said surfaces, said coupling medium incorporating therein a thermally sensitive agent that has a color depending on the temperature to which said medium is subjected;

stabilizing said coupling medium to the initial temperature of said body surface at which said medium has a reference color;

placing said probe surface substantially in contact with a limited area of said body surface while said coupling medium is positioned therebetween;

radiating ultrasonic energy to said body by means of said probe, said radiated energy being adapted to dissipate heat on said limited area of said body surface; and adjusting the acoustic intensity of said radiated energy when there is a predetermined color change of said coupling medium relative to said reference color;

whereby the acoustic intensity of the ultrasonic energy applied to said body is monitored through the effect on said thermally sensitive agent produced by the heat dissipated on said limited body surface area.

* * * * *

UNITED STATES PATENT AND TRADEMARK OFFICE
CERTIFICATE OF CORRECTION

PATENT NO. : 4,323,077
DATED : April 6, 1982
INVENTOR(S) : Lowell Scott Smith

It is certified that error appears in the above—identified patent and that said Letters Patent is hereby corrected as shown below:

On the cover sheet

In the list of U.S. Patent Documents, the last should read:

4,211,949   7/1980   Brisken et al ... 310/322

Column 4, line 25, "$10^2$ watt per $cm_2$" should read -- $10^{-2}$ watt per $cm^2$ --

Claim 1, line 1, after "method" insert -- of --

Signed and Sealed this

Twentieth Day of July 1982

[SEAL]

Attest:

Attesting Officer

GERALD J. MOSSINGHOFF

Commissioner of Patents and Trademarks